United States Patent
McNamara et al.

(10) Patent No.: US 6,254,550 B1
(45) Date of Patent: Jul. 3, 2001

(54) PREFORMED WIRE GUIDE

(75) Inventors: Thomas O. McNamara, Los Angeles, CA (US); Beth A. Kirts; Edward J. Morris, both of Bloomington, IN (US)

(73) Assignee: Cook Incorporated, Bloomington, IN (US)

(*) Notice: Subject to any disclaimer, the term of this patent is extended or adjusted under 35 U.S.C. 154(b) by 0 days.

(21) Appl. No.: 09/377,293

(22) Filed: Aug. 19, 1999

Related U.S. Application Data

(60) Provisional application No. 60/097,056, filed on Aug. 19, 1998.

(51) Int. Cl.$^7$ .............................. A61B 5/00; A61M 25/00
(52) U.S. Cl. ............................................................ 600/585
(58) Field of Search ............................ 600/585; 606/213, 606/159

(56) References Cited

U.S. PATENT DOCUMENTS

| | | |
|---|---|---|
| 4,548,206 | 10/1985 | Osborne . |
| 4,665,906 | 5/1987 | Jervis . |
| 4,854,330 | 8/1989 | Evans, III et al. . |
| 4,867,174 | 9/1989 | Skribiski . |
| 4,917,102 | 4/1990 | Miller et al. . |
| 4,925,445 | 5/1990 | Sakamoto et al. . |
| 4,934,380 | 6/1990 | de Toledo . |
| 4,935,068 | 6/1990 | Duerig . |
| 4,976,691 | 12/1990 | Sahota . |
| 4,994,069 | 2/1991 | Ritchart et al. . |
| 5,069,217 | 12/1991 | Fleischhacker, Jr. . |
| 5,069,226 | 12/1991 | Yamauchi et al. . |
| 5,122,136 | 6/1992 | Guglielmi et al. . |
| 5,131,406 | 7/1992 | Kaltenbach . |
| 5,147,370 | 9/1992 | McNamara et al. . |
| 5,171,383 | 12/1992 | Sagae et al. . |
| 5,184,621 | 2/1993 | Vogel et al. . |
| 5,190,546 | 3/1993 | Jervis . |
| 5,234,003 | 8/1993 | Hall . |
| 5,234,437 | 8/1993 | Sepetka . |
| 5,238,004 | 8/1993 | Sahatjian et al. . |

(List continued on next page.)

FOREIGN PATENT DOCUMENTS

| | | |
|---|---|---|
| 0550258 | 7/1993 | (EP) . |
| 0820782 | 1/1998 | (EP) . |
| 9115152 | 10/1991 | (WO) . |
| 9406503 | 3/1994 | (WO) . |

Primary Examiner—Cary O'Connor
Assistant Examiner—Brian Szmal
(74) Attorney, Agent, or Firm—Richard J. Godlewski; Anton P. Ness

(57) ABSTRACT

A preformed anchoring wire guide (10) for medical procedures such as renal angioplasty. The wire guide (10) is comprised of a superelastic memory alloy mandril (11), such as a nickel-titanium alloy, and includes a preformed bend (14) having an angle (15) with respect to the longitudinal axis (28) that corresponds with the takeoff angle of the renal artery (23) relative to the aorta (33). This preformed bend (14) allows easier access to the ostium (22) of the renal artery (23) and allows the distal portion (27) of the wire guide to anchor within the artery (23) and resist dislodgement and deformation, thereby improving trackability of a balloon angioplasty catheter (21), reducing the need for a guiding catheter, and reducing the likelihood of vessel damage or thrombus shear due to forces that are normally exerted against the wall of the vessel (33) by a standard wire guide. The wire guide has a tapered distal portion (20) over which a spring coil wire (16) is attached to provide radiopacity and safety to the vasculature. The distal portion (27) of the wire guide is flexible and is further made atraumatic by the addition of a hook-shaped or "J" tip (29). Additionally, the nickel-titanium alloy mandril is cold-worked in its austenitic phase at preformed bend (14) by overstressing the wire in a fixture, thereby shifting at least part of the crystalline structure to martensite within the region of the preformed bend (14).

26 Claims, 3 Drawing Sheets

U.S. PATENT DOCUMENTS

| | | |
|---|---|---|
| 5,242,759 | 9/1993 | Hall . |
| 5,243,996 | 9/1993 | Hall . |
| 5,246,007 | 9/1993 | Frisbie et al. . |
| 5,250,071 | 10/1993 | Palermo . |
| 5,261,916 | 11/1993 | Engelson . |
| 5,269,793 * | 12/1993 | Simpson ............................. 606/159 |
| 5,295,493 * | 3/1994 | Radisch, Jr. ........................ 600/585 |
| 5,345,937 | 9/1994 | Middleman et al. . |
| 5,358,479 | 10/1994 | Wilson . |
| 5,365,943 | 11/1994 | Jansen . |
| 5,368,049 | 11/1994 | Raman et al. . |
| 5,411,476 | 5/1995 | Abrams et al. . |
| 5,488,959 | 2/1996 | Ales . |
| 5,488,960 | 2/1996 | Toner . |
| 5,542,434 * | 8/1996 | Imran et al. ........................ 128/772 |
| 5,558,101 | 9/1996 | Brooks et al. . |
| 5,578,074 | 11/1996 | Mirigian . |
| 5,597,378 | 1/1997 | Jervis . |
| 5,624,508 | 4/1997 | Flomenblit et al. . |
| 5,720,300 | 2/1998 | Fagan et al. . |
| 5,725,534 | 3/1998 | Rasmussen . |
| 5,725,570 | 3/1998 | Heath . |
| 5,749,370 | 5/1998 | Brooks et al. . |
| 5,749,890 | 5/1998 | Shaknovich . |
| 5,797,857 | 8/1998 | Obitsu . |
| 5,827,202 * | 10/1998 | Miraki et al. ....................... 600/585 |
| 5,843,002 * | 12/1998 | Pecor et al. ......................... 600/585 |
| 5,853,421 * | 12/1998 | Leschinsky et al. ................ 606/213 |
| 5,924,998 * | 7/1999 | Cornelius et al. ................... 600/585 |
| 6,001,068 | 12/1999 | Uchino et al. . |
| 6,132,389 | 10/2000 | Cornish et al. . |
| 6,139,510 | 10/2000 | Palermo . |

\* cited by examiner

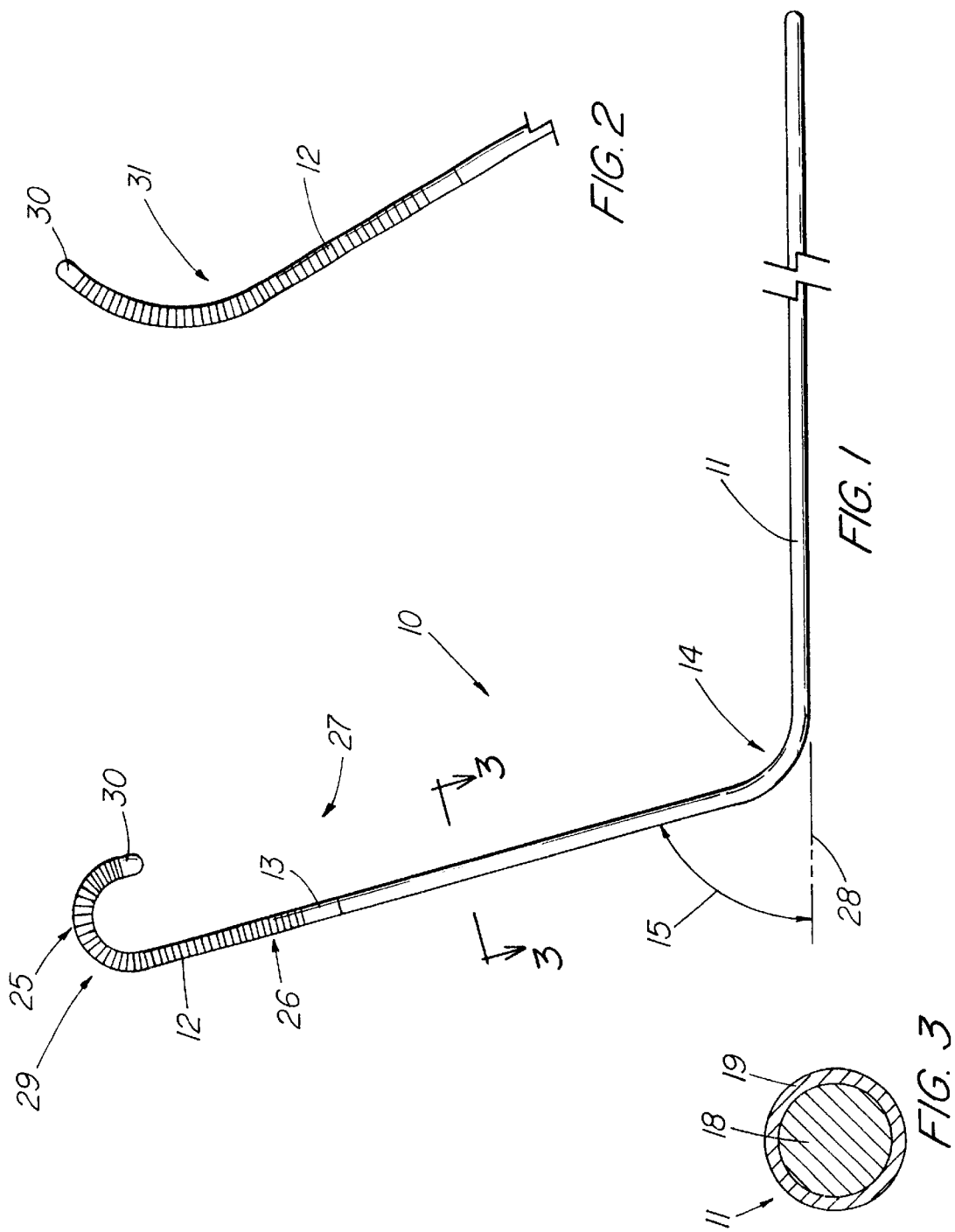

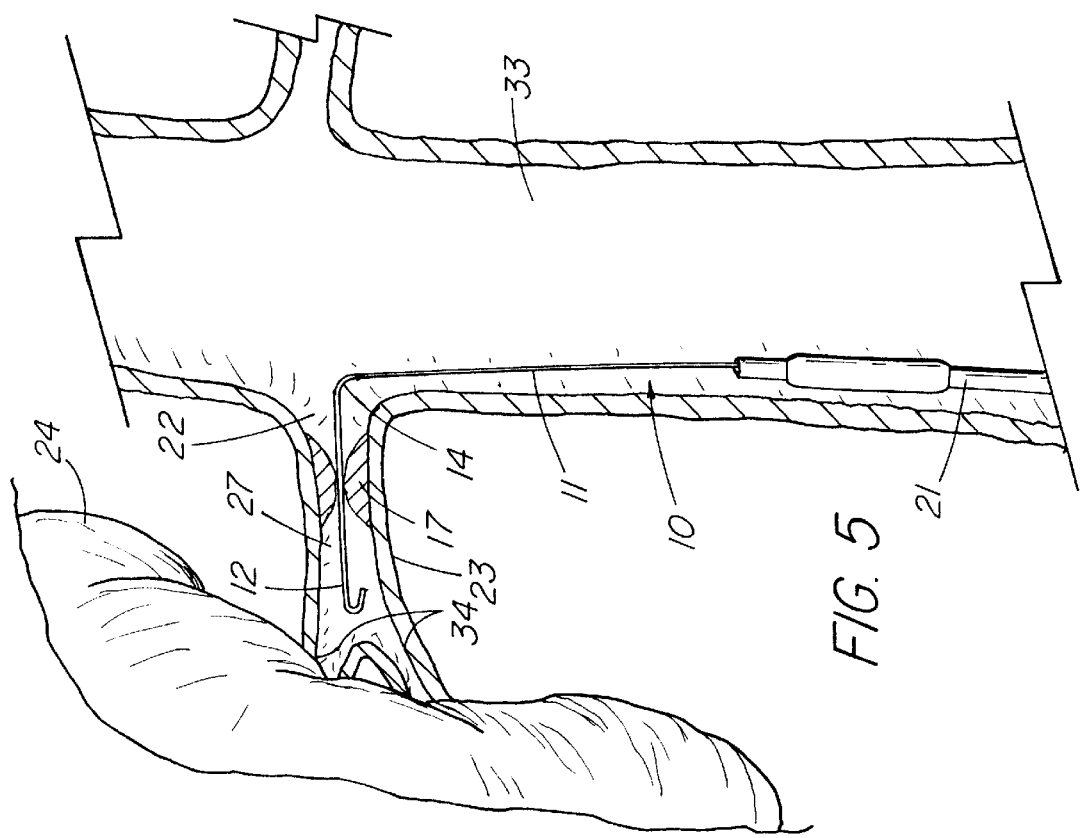
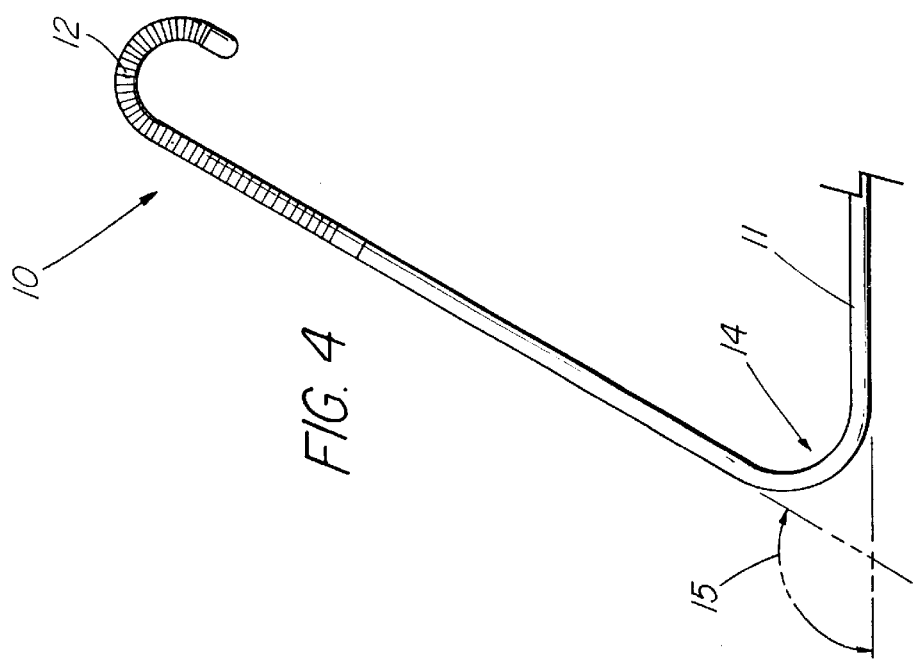

PREFORMED WIRE GUIDE

CROSS-REFERENCE TO RELATED APPLICATIONS

This application claims priority of provisional application Ser. No. 60/097,056, filed Aug. 19, 1998.

TECHNICAL FIELD

This invention relates generally to medical devices and, in particular, to a wire guide.

BACKGROUND OF THE INVENTION

Balloon angioplasty, a medical procedure by which an occluded or narrowed blood vessel is dilated and reopened using an inflatable balloon mounted on a catheter, was pioneered by Andreas Greuntzig in the 1970's. The coronary version of this new procedure, Percutaneous Transluminal Coronary Angioplasty (PTCA), soon became recognized as a highly effective method of treating diseased coronary artery disease. More recently, angioplasty has become a standard approach for treatment of renal artery stenoses. Percutaneous Transluminal Renal Angioplasty (PTRA), with its low rate of complications, has now largely replaced surgery as treatment for renal artery stenoses, which are common contributing factors in patients diagnosed with arterial hypertension, renal insufficiency, or cardiac insufficiency.

The basic angioplasty procedure usually involves percutaneously introducing a guiding catheter through an introducer sheath to the target site and then engaging the ostium of the vessel. A wire guide is fed through the guiding catheter and ostium where it is placed across the lesion in the vessel. Finally, a balloon catheter is introduced over the wire guide and positioned at the lesion to dilate the vessel. Increasingly more often, a stent is also placed following balloon dilatation to prevent restenoses of the lesion. One procedure for placing the balloon catheter at the treatment site is known as the "Push-Pull" Technique whereby the physician advances the balloon catheter through the guiding catheter ("push") while applying slight forward pressure to the latter. At the same time, an assistant holds the proximal end of the wire guide, providing gentle traction ("pull"). Care must be taken during the advancement of the catheter to avoid dislodging the wire guide from the treatment site. This is especially of concern during a renal procedure due to the relatively short length of the renal artery and the acute angle of the artery relative to the aorta.

The unique anatomy of the renal vessels presents difficulties when using existing wire guides for PTRA. Many physicians select wire guides developed for coronary procedures which are designed to facilitate negotiation of tortuous vessels and minimize trauma to small delicate coronary arteries. Because of their required flexibility, coronary wire guides usually lack the desired stiffness for PTRA. A stiffer wire guide permits better tracking by the catheter over the wire. However, a stiff wire guide can also subject the vasculature to forces during manipulation that are capable of perforating the vessel or injuring the ostial takeoff from the aorta into the renal vessel. The wire guide receives much of the up and down stresses during the procedure and transfers them to the vessel wall. These same stresses are often responsible for dislodging the distal end of the wire guide from the orifice, necessitating withdrawal of the catheter and reintroduction of the wire guide. If the wire guide enters the ostium of the vessel at the correct angle, the stresses are instead received by the catheter, thus protecting the fragile vessel. Furthermore, the typical stresses at that site during manipulation of a straight wire can also cause thrombus to shear from the vessel wall, often leading to an embolus and related serious complications.

SUMMARY OF THE INVENTION

The foregoing problems are solved and a technical advance is achieved in an illustrative preformed wire guide having a flexible tip portion that is atraumatic to the vessel as the wire guide is advanced, the flexible tip portion having a distal tip and a proximal portion that includes a preformed bend approximating the takeoff angle of a vessel, for example, a renal artery relative to the aorta from which it branches. By producing a wire guide with the correct anatomical preformed bend, there is much less risk of trauma to the vessel. A related benefit of the present invention is lowering the risk of displacing thrombus that often forms just inside the ostium, especially in the presence of a stenotic lesion. A straight wire would receive much of the force at the turn into the ostium created by the advancing catheter and potentially transfer much of that force to the wall of the vessel. By forming the bend in the wire guide, the forces created from the catheter tracking over the wire are exerted on the catheter itself and not to the vessel wall where injury or disruption of thrombus can occur. Nitinol can be permanently shaped by annealing with extreme heat, or by cold-working which involves overstressing the wire. To produce a more rigid bend segment for protecting the vessel, cold working the nitinol mandril is preferred over the annealed embodiment which exhibits less resistance to the tracking forces of the catheter.

The second major benefit of having an anatomically shaped preformed bend is providing a portion of the wire guide to serve as an anchor to maintain the device within the vessel during advancement of a catheter over the wire. A straight wire guide would be much more likely to become dislodged during the course of tracking the catheter to the treatment site.

In a preferred embodiment of the illustrative invention, the flexible tip portion includes a spring coil wire that is attached over a solid wire mandril. The transition between the highly-flexible atraumatic tip and the stiffer mandril is relatively abrupt, compared to typical wire guides, due to the short available length of vessel in which the anchoring portion of the mandril can reside and the need for that mandril to be of sufficient stiffness to maintain a proper anchor. A bend having a preferred range of 30° to 150° formed in the mandril wire allows the wire guide to more easily enter the ostium of the renal artery or vein, depending on the particular anatomy of the patient, and whether a superior or inferior approach is used. A more preferred range of bend angles is 45° to 135°, with the most preferred range being 60° to 120°. The improved ability to access the renal vessel can reduce the need for using a guiding catheter to place the wire guide, thereby eliminating a step of the procedure and the attendant risks.

The solid mandril wire is of sufficient stiffness to retain the anatomical preformed bend and allow the wire guide to remain anchored in the vessel while a catheter is being fed over the wire. In the preferred embodiment of the invention, the mandril wire is made of a superelastic material such as a nickel-titanium (Ni—Ti) alloy (commercially available as nitinol). The bend in the mandril is formed by mechanically stressing (cold working) and plastically deforming the wire while in its austenitic state to create at least a partial localized zone of martensite. The nitinol wire can be made relatively thin while still retaining the preformed bend and the requisite stiffness. Other possible materials for the mandril include elastic biocompatible metals such as stainless steel, titanium, or tantalum.

While the potential benefits of cold working nitinol wire to plastically deform the original shape have not been fully appreciated by manufacturers of wire guides and other medical devices, there are two primary advantages over the standard annealing method. The first involves the differences in how the device behaves as bending stresses are applied. In the absence of applied stress, the annealed wire guide is completely in an austenitic state, even in the curved regions. When sufficient stress is applied anywhere upon the length of the device, the face-centered crystals of the austenitic material shift to martensite until the stress is removed. Thus, the bend and straight portions of the annealed wire guide have very similar flexural properties. In contrast, the cold-worked wire guide is comprised of regions of both austenite and martensite along its length. Consequently, the preformed bend of a cold-worked renal wire guide remains in at least a partial martensitic state and does not exhibit the unusual superelastic phenomenon that occurs during an austenitic to martensitic transformation.

To provide maximum protection to the renal vessels during a procedure, the flexible tip portion of the preferred embodiment has a curved shape. The "J"-tip of the illustrative embodiment protects the vessel and delicate tissues as the wire guide is advanced into the renal vein. A curved shape tip is more easily deflected and prevents the stiff mandril wire from exerting a dangerous amount of force against the vessel wall. The transition from a flexible tip to the stiffer mandril is achieved by soldering the spring coil tip to the tapered end of the mandril at the point where the taper begins. The tapered distal end of the mandril provides the overlapping coiled portion with a diminishing degree of stiffness toward its distal end.

In the illustrative embodiment, a polymer coating is added to the mandril of the wire guide for improved lubricity. Polytetrafluoroethylene (PTFE) is the preferred material, however, hydrophilic coatings such as SLIP-COAT™ (Sterilization Technical Services, Inc., Rush, N.Y.) can be used as an alternative material as well as other lubricious coatings or coating materials.

BRIEF DESCRIPTION OF THE DRAWING

FIG. 1 depicts a side view of the illustrative wire guide of the present invention;

FIG. 2 depicts an alternative embodiment of the flexible tip portion of the wire guide of FIG. 1;

FIG. 3 depicts a cross-sectional view of the embodiment of FIG. 1 along line 3—3;

FIG. 4 depicts a second preferred embodiment of the illustrative wire guide of the present invention;

FIG. 5 depicts a schematic view of a third embodiment of the wire guide of the present invention located within the renal system of a patient;

DETAILED DESCRIPTION

Figure 6:
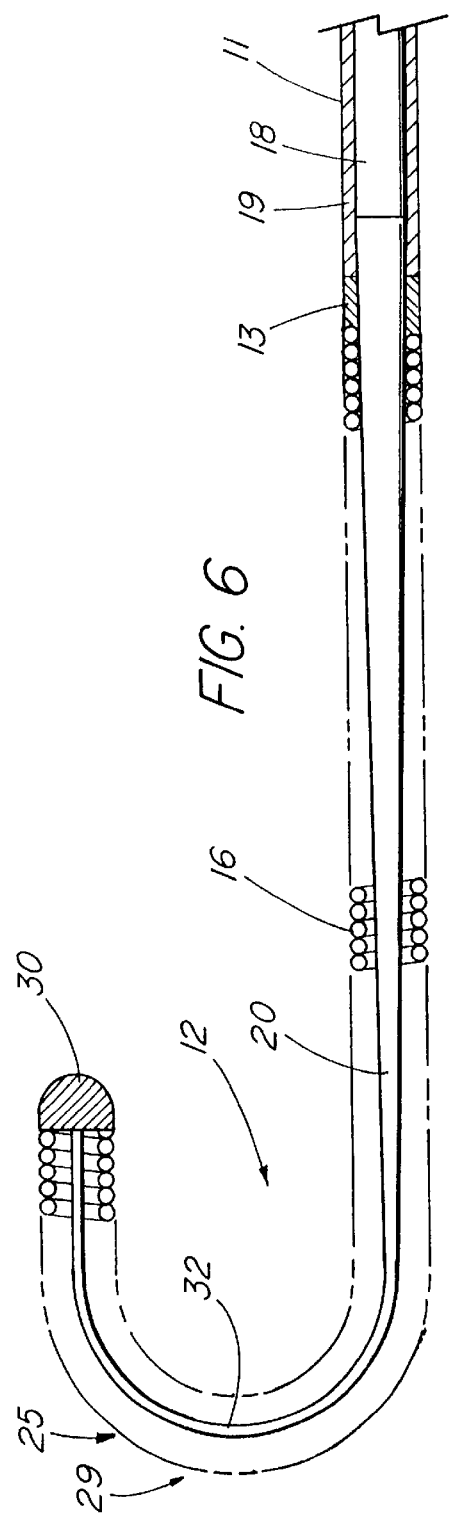
FIG. 6 depicts an enlarged, partially sectioned side view of the distal portion of the wire guide of FIG. 1, and FIG. 7 graphically depicts stress-strain curves for cold-worked nitinol wire and for annealed nitinol wire.

FIG. 1 depicts a side view of an illustrative embodiment of wire guide 10 of the present invention. The wire guide 10 includes both a mandril 11 and a tip portion 12, preferably a flexible tip portion 12, extending proximally from the distal tip 30 of the wire guide. In the preferred embodiment, the mandril 11 extends the entire length of the wire guide with distal end 25 of the flexible tip portion 12 extending from distal tip 30 of the wire guide to proximal end 26 of the flexible tip portion 12 and to solder joint 13. The mandril 11 include extends through a preformed bend 14 that marks the beginning of a distal portion 27 of the wire guide. Angling the distal portion 27 facilitates entry of the wire guide into the ostium of the renal artery. The distal portion 27 becomes an anchor to help prevent dislodgment of the wire after it has been placed. The wire guide is also anatomically shaped for procedures involving the renal vein, however these are far less common. The takeoff of the renal artery from the aorta varies in its angle. Therefore, it is contemplated that the wire guide be made available with different bend angles to accommodate the normal variation in patient anatomy. An additional factor is that the wire guide can be introduced using either an inferior approach via the femoral artery (preferred) or a superior approach, typically via a brachial access site. The wire guide bend angles can range from 30° to 150°, with a more preferred range of 45° to 135°. The distal portion 27 of the first illustrative embodiment is bent at an angle 15 of approximately 60° relative to the longitudinal axis 28 of the wire guide 10. A second embodiment depicted in FIG. 4 has a preformed bend 14 with an angle 15 of approximately 120°. Together, these two embodiments represent the most common, and therefore, most preferred range of angles for accessing the renal artery. A third preferred embodiment is depicted in FIG. 5 whereby the distal portion 27 of the wire guide 10 is formed at a 90° angle.

In the preferred embodiment, the portion of the mandril 11 proximal to the flexible tip portion 12 is comprised of a mandril core 18 and a microthin polymer outer coating 19 such as polytetrafluoroethylene (PTFE) as depicted in FIG. 3. Alternative coatings include hydrophilic materials such as SLIP-COAT™ polymers (Sterilization Technical Services, Inc., Rush, N.Y.) or other polymers that have been surface treated to increase lubricity. Preferably, the mandril core 18 includes material having superelastic properties such as the Ni—Ti alloy commercially known and available as nitinol. Nitinol is comprised of nearly equal parts of nickel and titanium and can also include small amounts of other metals such as vanadium, chromium, or iron to affect the physical properties of the alloy. The preferred nitinol formulation for this application has a martensitic to austenitic transformation temperature below body temperature, and most preferably, below normal room temperature. The remarkable ability of a superelastic alloy to return to its predetermined shape when subjected to stress, makes it an excellent material for this application. Although stainless steel and other non-superelastic materials can be used, they are less resilient. In the case of the present invention where the shape of the wire guide is matched to the anatomical site in which it is used, the plastic deformation that can occur with ordinary metal wires during manipulation can affect the efficacy of the device. In addition to nitinol, superelastic or pseudoelastic copper alloys, such as Cu—Al—Ni, Cu—Al—Zi, and Cu—Zi are available as alternative wire guide materials. The preferred diameter for the wire guide ranges from about 0.010 to 0.035 in. with a diameter of approximately 0.018 in., mostly comprised of the nitinol metallic core 18, being generally preferred when using a single diameter wire guide. Another embodiment includes making the mandril 11 larger in diameter, e.g., 0.023 in., and attenuating the tip 12 to 0.018 in. The larger mandril provides better positional support for placement in the renal vessel, while attenuation of the distal portion 27 advantageously provides a substantially atraumatic tip. The coating 19, which is approximately 0.003 in.±0.001 thick in the illustrative embodiment, serves to lower the coefficient of friction and ease manipulation of the wire guide within the vessel or guiding catheter, if the latter is used.

Because of the superelasticity of nitinol, permanently deforming the material to produce the desired bend in the wire requires special manufacturing techniques. The standard method of forming nitinol into a desired shape is disclosed in U.S. Pat. Nos. 5,597,378 and 4,665,906 to Jervis, both entitled "Medical Devices Incorporating SIM Alloy Elements", which is herein incorporated by reference. The basic procedure involves maintaining the device in the desired final shape while subjecting it to extreme heat for a prescribed period of time. Stressing the wire guide under annealing temperatures "locks" the curve in an austenitic state. When the annealed wire guide is deflected, there is a localized, transient shift of the austenitic material to martensite, known as stress-induced martensite (SIM). While annealing represents a viable method of producing the specific bend in the present invention, the preferred method involves cold working the wire guide, i.e., reshaping the wire guide by the application of sufficient mechanical force to permanently shift a portion of the crystalline structure of the nitinol from austenite to martensite within the region of the preformed bend. Given the high degree of resilience of the austenitic nitinol, the stress required to permanently deform the device to the degree required is considerable. One method of cold working the nitinol wire involves using a fixture or forming tool which holds the wire and includes a pin around which the wire is deformed into a much tighter angle than the final angle. The diameter of the pin, the position of wire within the fixture, and the degree of force applied determine the tightness of the resulting bend. By using predetermined wire and fixture parameters, it is possible to achieve a predictable angle of bend using such a forming tool to overstress the nitinol wire.

Figure 7:
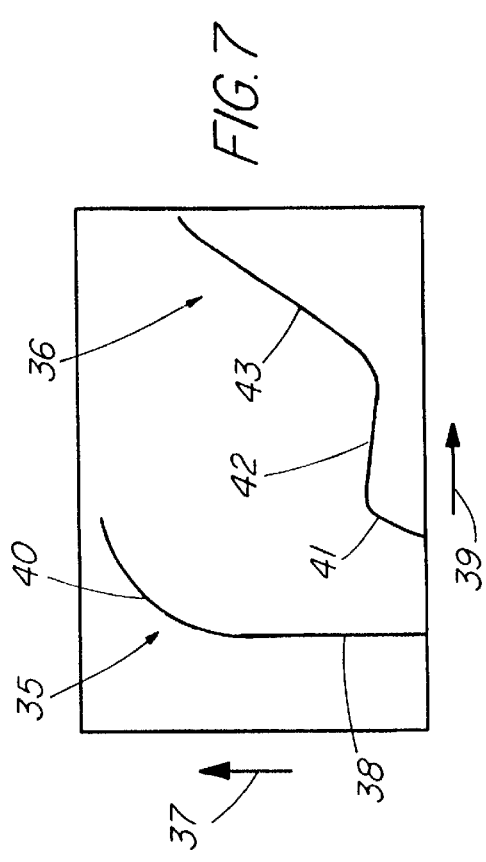

FIG. 7 graphically depicts the generalized stress-strain curves 35 and 36 for similar wires made from cold-worked nitinol and annealed nitinol 35 and 36, respectively. As stress 37 is applied to the cold-worked nitinol wire 35, there is an initial resistance 38 to the increase in strain 39. At a point 40 in the cold-worked nitinol curve, further stress produces a more linear increase in strain. The annealed nitinol curve 36 exhibits the traditional SIM stress-strain curve whereby following an initial resistance to strain exhibited by portion 41 of the curve, the material enters the stress-induced martensitic phase, depicted by portion 42 of the curve. During this SIM phase, the device can continue to deflect (strain) with minimal application of additional stress. At a certain point in the curve 43, the stress-strain relationship for the material becomes much more linear. Both processes produce a device with nitinol's superelastic properties, yet the preformed bend of the annealed device becomes highly flexible when subjected to stress and undergoes the phase change. The stiffer preformed bend of the cold-worked device is ideal for the renal wire guide because of its dual function as an anchor into the renal artery and a track over which a catheter is guided. While increased flexibility can be an advantage for certain medical applications, a more flexible annealed wire guide would be more likely to dislodge from the vessel as the PTRA balloon catheter is tracking over the guide. The second advantage of cold working the bend of the wire guide of the present invention is that stock polymer-coated nitinol wire can be used to manufacture the finished device. The high temperatures required to produce the annealed wire guide preclude using the pre-coated wire stock since the polymer coating cannot withstand the temperatures used in the annealing process. This means that virtually any coatings or treatment must be performed by the manufacturer as a final step. Cold working allows a manufacturer the flexibility to purchase pre-coated nitinol wire stock, easily customizing the shape of the stock or existing straight wire guides for a given application, and doing so at a lower cost.

The flexible tip portion 12 of the wire guide 10 provides a distal tip 30 that is atraumatic to the vessel and far less likely to damage delicate tissues during introduction and positioning of the wire guide. In the illustrative embodiment, the flexible tip portion 12 comprises a segment of spring coil wire 16 with closely adjacent turns. Platinum wire is used to make the distal end of the device highly visible under fluoroscopy. Other possible radiopaque materials include gold, tantalum, or tungsten. Radiolucent materials such as stainless steel can also be used. The poor imaging disadvantage can be overcome if a second radiopaque material is used in conjunction with the stainless steel such as at the tip or being interwound with the stainless steel coil. A surface treatment can also be used to make the coil radiopaque or echogenic. The distal tip 30 of the coiled flexible portion terminates in a solder tip that is ground into a rounded shape and then buffed to minimize potential trauma. The solder joint 13 that joins the coiled, flexible portion to the mandril is made through a process that is fully described in U.S. Pat. No. 5,242,759 to Hall entitled, "Joint, a Laminate, and a Nickel-Titanium Alloy Member Surface for Bonding to Another Layer of Metal", which is herein incorporated by reference.

Preferably, the distal end 25 of the flexible tip portion 12 includes a curve 31 to reduce the likelihood of trauma caused from the advancing wire guide. In the illustrative embodiment, the curve 31 comprises a hook-shaped tip 29, such as a "J" or "Shepherd's crook". Directing the distal tip 30 of flexible portion away from the distal end 25 of the wire guide provides a higher degree of protection against damaging tissue compared to the concentrated force that is potentially exerted by a forward-directed tip, even though the tip is made to flex with contact. FIG. 2 depicts an alternative atraumatic flexible tip portion 12 that contains a curve 31 of approximately 45° that causes the distal tip 30 to laterally deflect when it encounters resistance.

FIG. 6 depicts an enlarged, partially sectioned side view of the flexible tip portion 12 of the illustrative wire guide 10 of FIG. 1. In the preferred embodiment shown, one end portion 20 of the mandril 11 includes a tapered distal portion 20 wherein the taper begins at the point 13 at where the coiled, flexible tip portion 12 is soldered to the mandril. The taper continues to soldered distal tip 30 at the distal end of the mandril. The taper is produced by performing a centerless grind of the nitinol core 18, a process which also removes the existing PTFE coating. In the preferred embodiment, the reduction in diameter of the tapered distal portion 20 is gradual across its entire length. Alternatively, the overall taper can be accomplished in a stepped manner with an alternating series of tapered and straight portions. The taper both permits the flexible portion to attach relatively flush to the coated mandril wire such that the outside diameter of the wire guide remains constant across its entire length, and imparts an increasing degree of flexibility to the flexible portion of the wire guide. In an embodiment in which the flexible portion has a smaller diameter than the mandril core, the taper of the mandril normally begins prior to the attachment point of the flexible portion. While the flexible portion can be soldered to the distal end of the mandril, usually making a standard safety wire necessary so that the flexible portion remains secured to the mandril, the result would be a tip of uniform flexibility that would provide less protection to the patient from the much stiffer advancing mandril wire. The coiled wire 16 of the flexible tip portion 12 assumes the shape of the shaped tapered distal portion 20 and would otherwise comprise a straight segment at the distal end of the device.

Creating a curve 31 such as the "J"-shaped hook 29 at the distal end 25 of the wire guide is accomplished in similar manner as the anatomical preformed bend 14 of the mandril (depicted in FIG. 1). If the core comprises nitinol, the distal tapered portion 20 is formed into a curve 31 by overstressing the wire over a forming tool to produce the desired final preformed bend. As with the more proximal anatomical preformed bend 14, the distal bend 32 in the tapered nitinol portion 20 undergoes at least a partial localized phase shift to martensite due to the mechanical stress. Similarly, the distal bend 32 in the tapered portion differs in structure from stress-induced martensite produced by the combination of heat and mechanical stress, although the latter technique is also an alternative method of forming the distal bend 32. Although there are benefits to having a coiled, flexible tip at the distal end, namely providing radiopacity and allowing the distal portion of the device to have the same diameter as the mandril portion, a wire guide that lacks the coiled portion would represent a viable alternative embodiment. The primary requirement is that the distal portion is sufficiently flexible to be atraumatic to tissue, whether by tapering or other structural modifications.

FIG. 5 depicts a partially-sectioned view of the wire guide 10 of the present invention placed within the renal anatomy of a patient to illustrate its use. As shown, the distal portion 27 of the wire guide is anchored within the renal artery 23 which supplies the right kidney 24. The preformed bend 14 of mandril portion 27, which is at a 90° angle in this particular embodiment, is situated at the ostium 22 where the aorta 33 feeds into the renal artery. The flexible tip portion 12 of the wire guide lies distal to the ostium 22 within the renal artery 23 and usually extends to a point proximal to where the renal artery branches to form the interlobar arteries 34. The distal portion 27 of the wire guide, approximately 3 to 13 cm length and most preferably around 7 cm for most patients, provides a firm anchor to resist dislodgment when a PTRA catheter 21 is fed over the wire to dilate a stenosis 17 of the renal artery. This is especially critical as the advancing catheter nears the ostium 22.

Any undisclosed or incidental details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of even rudimentary skills in this area, in view of the present disclosure.

What is claimed is:

1. A wire guide comprising:
 a mandril of superelastic material, and
 a tip portion disposed at an end portion of the mandril, wherein the mandril extends through at least one preformed bend disposed proximate to the tip portion for anchoring the wire guide in a vessel, wherein the preformed bend includes a localized martensitic region.

2. The wire guide of claim 1, wherein the superelastic material of the mandril is in the austenitic phase except for the localized martensitic region.

3. The wire guide of claim 1, wherein the tip portion is flexible, thereby being atraumatic to the vessel when introduced therein, wherein the end portion comprises a tapered distal portion of the mandril and includes the preformed bend, and wherein the tip portion is connected to the tapered distal portion of the mandril.

4. The wire guide of claim 3, wherein the flexible tip portion includes spring coil wire disposed about the tapered distal portion.

5. The wire guide of claim 3, wherein the flexible tip portion includes a curved shape.

6. The wire guide of claim 3, wherein the flexible tip portion includes a hook shape.

7. The wire guide of claim 1, wherein the superelastic alloy is a nickel-titanium alloy.

8. The wire guide of claim 7, wherein the preformed bend includes a localized austenitic region and a martensitic region, the martensitic region being produced from cold working the mandril.

9. The wire guide of claim 1, wherein the martensite of the localized martensitic region is mechanically-induced martensite.

10. The wire guide of claim 1, wherein the preformed bend is induced by mechanical deformation of the mandril such that the superelastic material of the preformed bend includes a martensitic crystalline structure, while non-mechanically deformed portions of the mandril comprise a substantially austenitic crystalline structure.

11. The wire guide of claim 1, wherein the mandril further includes a polymer coating at least proximally from the tapered distal portion.

12. The wire guide of claim 1, wherein the preformed bend forms an angle with respect to a longitudinal axis of the mandril of between 30 and 150 degrees.

13. The wire guide of claim 1, wherein the preformed bend forms an angle with respect to a longitudinal axis of the mandril of between 45 and 135 degrees.

14. The wire guide of claim 1, wherein the preformed bend forms an angle with respect to a longitudinal axis of the mandril of between 60 and 120 degrees.

15. A wire guide comprising:
 a mandril of superelastic material and extending through a preformed bend disposed therealong,
 a tapered distal portion of the mandril extending distally beyond the preformed bend for anchoring the wire guide in a second vessel of a patient that extends at a takeoff angle from a first vessel thereof,
 the tapered distal portion including a flexible tip portion, and
 a spring coiled wire attached to the mandril around and over the tapered distal portion and the flexible tip portion,
 wherein the preformed bend includes a localized martensitic region.

16. The wire guide of claim 15, wherein the superelastic alloy is a nickel-titanium alloy.

17. The wire guide of claim 16, wherein the preformed bend includes martensitic nitinol produced from cold-working the mandril.

18. The wire guide of claim 15, wherein the martensite of the localized martensitic region is mechanically-induced martensite.

19. The wire guide of claim 15, wherein the tapered distal portion includes a flexible tip portion having an atraumatic curved shape.

20. The wire guide of claim 15, wherein the mandril further includes a polymer coating at least proximally from the tapered distal portion.

21. The wire guide of claim 15, wherein the preformed bend forms an angle with respect to a longitudinal axis of the mandril of between 30 and 150 degrees.

22. The wire guide of claim 15, wherein the preformed bend forms an angle with respect to a longitudinal axis of the mandril of between 45 and 135 degrees.

23. The wire guide of claim 15, wherein the preformed bend forms an angle with respect to a longitudinal axis of the mandril of between 60 and 120 degrees.

24. A wire guide comprising:
- a mandril of superelastic material having a tapered distal portion and extending through a single preformed bend disposed along the tapered distal portion, the preformed bend having an angle of between 45 and 135 degrees with respect to the longitudinal axis of the mandril,
- the mandril further including a polymer coating at least proximally from the tapered distal portion,
- a distal end portion extending distally beyond the preformed bend for anchoring the wire guide in a second vessel of a patient that extends at a takeoff angle from a first vessel thereof, the distal end portion including a flexible tip portion having an atraumatic curved shape, and
- a spring coiled wire attached to the mandril around and over the tapered distal portion and the flexible tip portion,
- wherein the preformed bend includes a localized martensitic region produced from cold working the mandril while the remainder of the mandril is austenitic.

25. A metal member comprising:
- an elongate metal member of superelastic alloy,
- the member, while in an unconstrained configuration, extending through at least one preformed bend, the member being constrainable to a second configuration, whereby at release of external constraining forces, the member substantially returns to the unconstrained configuration, and
- the preformed bend further comprising mechanically-induced martensite.

26. The metal member of claim 25 wherein portions of said member other than said preformed bend are comprised of austenite.

* * * * *